United States Patent [19]
Tremblay et al.

[11] Patent Number: 5,900,539
[45] Date of Patent: May 4, 1999

[54] DEVICE AND METHOD FOR DETERMINING RHEOLOGICAL QUALITY OF NON-NEWTONIAN LIQUIDS

[75] Inventors: Bernard Tremblay, Edmonton; Mario De Rocco, Leduc; Rodney K. Ridley, Edmonton; Surindar Singh, Edmonton; Kerry Scott, Edmonton, all of Canada

[73] Assignee: Alberta Research Council, Edmonton, Canada

[21] Appl. No.: 08/900,855

[22] Filed: Jul. 25, 1997

[51] Int. Cl.⁶ .................................................. G01N 11/04
[52] U.S. Cl. .......................................... 73/54.13; 73/54.11
[58] Field of Search ............................ 73/54.11, 54.13, 73/54.14, 54.04, 54.07, 54.09

[56] References Cited

U.S. PATENT DOCUMENTS

| | | | |
|---|---|---|---|
| 2,780,096 | 2/1957 | Noble et al. | 73/156 |
| 3,242,720 | 3/1966 | Zavasnik | 73/56 |
| 3,758,776 | 9/1973 | Frohne et al. | 73/54.14 |
| 3,990,295 | 11/1976 | Renovanz et al. | 73/55 |
| 4,185,493 | 1/1980 | Feinstein | 73/56 |
| 4,313,339 | 2/1982 | Nichols et al. | 73/54.14 |
| 4,316,383 | 2/1982 | Fruman et al. | 73/55 |
| 4,437,337 | 3/1984 | Fenrick | 73/54 |
| 4,539,837 | 9/1985 | Barnaby | 73/54.09 |
| 4,680,958 | 7/1987 | Ruelle et al. | 73/56 |
| 5,209,107 | 5/1993 | Grudzien, Jr. et al. | 73/54.14 |

*Primary Examiner*—Michael Brock
*Attorney, Agent, or Firm*—Neil Teitelbaum & Associates

[57] ABSTRACT

A method for evaluating rheological properties of certain non-Newtonian liquids employs the principle of a multiple forced flow of a single sample of the liquid through an orifice, thus effecting a significant elongation of the sample. The liquid is forced through the orifice by means of a piston. Preferably, the orifice is built into the piston so that the liquid remains stationary during the piston advance. The timing and rate of the sequential strokes of the piston are controlled and the differential pressure across the orifice is measured. A function between the timing of the piston strokes, the stroke rate and the differential pressure can be determined. The function has been found to represent a relatively reliable rheological "signature" of the tested liquid.

23 Claims, 9 Drawing Sheets

WATER-BASED GEL numbers above peaks = piston velocity (cm/sec)

WATER-BASED GEL numbers above peaks = piston velocity (cm/sec)

WATER-BASED GEL numbers above peaks = piston velocity (cm/sec)

DIESEL-BASED GEL numbers above peaks = piston velocity (cm/sec)

DIESEL-BASED GEL numbers above peaks = piston velocity (cm/sec)

DEVICE AND METHOD FOR DETERMINING RHEOLOGICAL QUALITY OF NON-NEWTONIAN LIQUIDS

FIELD OF THE INVENTION

This invention relates to a method and device for determining certain rheological properties of liquids, particularly non-Newtonian liquids.

BACKGROUND OF THE INVENTION

Many liquids (or semi-liquids) such as solutions of proteins, polymers and certain gels are non-Newtonian in behaviour and show relaxation effects and even non-linear response to deformation. For such liquids, viscosity measurement proves a difficult task as the rheological properties may change in response to the deformation of the measured quantity of the gel, not only to its temperature and pressure. Standard viscosity measurement methods cannot therefore be relied on to provide a quantitative measure ("signature") of the rheological properties of such liquids.

Fracturing gels are examples of non-Newtonian liquids. Fracturing gels are injected at a high pressure in oil or gas reservoirs to form fractures a few centimeters wide and several meters long. Coarse sand (proppant) is normally mixed with the gel to keep the crack open after the injection is stopped. The gel must have the correct yield stress, or strength, to carry the proppant. However, the gel should not be too viscous to inject. In other words, high gel strength is advantageous for carrying the proppant, but is a disadvantage for the purpose of injecting the gel.

Fracturing gels are usually prepared in the field. It is important, for the above reasons, that the rheological characteristics (yield and flow) of the gel prepared in situ be at least similar as those of the gel prepared in an off-site laboratory.

It is therefore desirable to determine, preferably on the site of the exploration, whether the particular gel has a proper strength, within acceptable limits.

Absolute methods of testing viscosity of liquids (Stokes' law, capillary tube, rotating cylinder and oscillating disc methods) are not suitable for fracturing gels. Other methods presently used for such gels (shear rheometer, Marsch funnel, vortex closure test and the lip test) do not give reliable repetitive results. In the shear rheometer, the gel slips on the walls of the cup and the bob. The Marsch funnel only works for less-viscous (weaker) gels which can flow through the funnel; the funnel test is basically qualitative and requires relatively low viscosity of the liquid measured. The lip test is qualitative as well.

Typically, a fracturing gel changes its rheological characteristics, and specifically undergoes strength reduction, upon deformation. The strength is at least partly regained with time, i.e. by allowing the gel to rest. Thus, a viscosity measurement based on a single flow of the gel through a capillary or the like may not give a proper representation of the rheological "signature" of the gel.

Various viscosimeters for liquids, including polymers and other non-Newtonian liquids, are described in the patent literature, e.g. U.S. Pat. Nos. 4,680,958 (Ruelle et al.); 5,289,728 (Johanson et al.); 4,316,383 (Fruman et al.); 4,185,493 (Feinstein); 3,990,295 (Renovanz et al.); and 2,780,096 (Noble et al.). Some of the devices rely on for example, measuring the time needed to expel under pressure an amount of liquid through a slot or outlet from a chamber. The devices described therein are still less than satisfactory for the purposes defined hereinabove since they do not take an allowance for a change of rheology of certain liquids such as fracturing gels as a function of deformation and relaxation of the liquid.

There is still a need for a method for reliable and quantitative testing of certain liquids such as fracturing gels and other non-Newtonian liquids where a change of the rheological properties of the liquid resulting from deformation and relaxation of the tested liquid is taken into account.

It is an object of the invention to develop a method for testing rheological properties of non-Newtonian liquids.

It is also an object of the invention to develop an apparatus for carrying out a determination of rheological properties of liquids, particularly non-Newtonian liquids, especially fracturing gels.

SUMMARY OF THE INVENTION

In accordance with the present invention, a method and apparatus are provided for enabling a determination of rheological characteristics of liquids, particularly non-Newtonian liquids, with greater reliability and reproducibility than heretofore. Basically, it has been found that for an acceptable determination of such characteristics, a single sample of the liquid should be forced through a defined narrow passage a number of times in measured time intervals, and the rheological characteristic of the liquid be measured at each passage e.g. in terms of pressure drop or time required for the passage. By using the same sample at each passage, the deformation and relaxation effects can be accounted for.

In accordance with one aspect of the invention, there is provided an apparatus for evaluating the rheological properties of a liquid, the apparatus comprising:

a chamber for accommodating a quantity of a liquid to be evaluated, a piston slidably movable within the chamber, drive means for moving the piston, control means associated with the drive means for controlling at least one parameter of the movement of the piston, an orifice in fluid communication with the chamber such that the liquid can pass through the orifice when the liquid is forced against it by a movement of the piston, measurement means for measuring a parameter of the flow of the liquid through the orifice, and data acquisition and processing means for evaluating said flow parameter as a function of the piston movement parameter, the function being indicative of the rheological properties of the liquid.

Preferably, the apparatus has a return flow passage arranged for returning the liquid expressed through the orifice back to the chamber.

In one embodiment of the invention, the control means are means for controlling the timing and the rate of the piston strokes when the liquid is forced by the piston against the orifice. The liquid sample is returned to its initial space and repeatedly passed through the orifice in timed intervals. The measurement means are means for measuring the differential pressure across the orifice which is then evaluated as a function of the piston stroke rate and timing, the function being indicative of the rheological properties of the liquid.

In another embodiment of the invention, the pressure of the piston is controlled when the liquid is forced by the piston against the orifice. The liquid sample is returned to its initial space and repeatedly passed through the orifice in timed intervals. The duration of the strokes, i.e. the time for the piston to move a predetermined distance within the chamber is measured, the time corresponding to a predetermined amount of the sample passing through the orifice. The time is measured over a number of strokes and a function of the time versus pressure is determined, the function being indicative of the rheological properties of the liquid.

In a specific embodiment of the invention, the apparatus comprises:

- a closable barrel adapted to receive a quantity of a liquid to be evaluated, the barrel having a first end and a second distal end,
- a piston slidable in said barrel between said first end and said second end, thus defining a first and a second chamber between said piston and the respective ends of the barrel,
- drive means for moving said piston between the first and the second end,
- control means associated with the drive means for controlling the speed and timing of the piston movement,
- an orifice associated with the piston and adapted for the liquid to pass therethrough from said first chamber to the second chamber when said liquid is pressured by the movement of the piston against it,
- return flow means for enabling the flow of the liquid back to the first chamber when the stroke of the piston is reversed,
- differential pressure measurement means for measuring the pressure drop across the orifice during the flow of the liquid through the orifice, and
- data acquisition and processing means for determining a relationship between the differential pressure and the at least one of the timing and the speed of the piston strokes, the relationship being indicative of rheological properties of the liquid.

In another aspect of the invention, there is provided a method for evaluating the rheological properties of a liquid utilizing an apparatus having a chamber for accommodating a quantity of a liquid to be evaluated, a piston slidably movable within the chamber, and an orifice in fluid communication with the chamber such that the liquid can pass through the orifice when the liquid is forced against it by a movement of the piston, the method comprising a) placing a sample of the liquid to be evaluated in the chamber, b) forcing the sample to flow through the orifice, c) repeating step b) a number of times while d) controlling at least one parameter of the piston movement and measuring a parameter of flow of the liquid through the orifice, and then e) determining a relationship between the flow parameter and the piston movement parameter, the relationship being indicative of the rheological properties of the liquid.

In an alternative embodiment, the method comprises the steps of:

a) placing a sample of the liquid to be evaluated in the chamber, b) forcing the sample to flow through the orifice, c) causing the sample to flow back into the chamber, d) repeating steps b) and c) while e) controlling at least one parameter of the piston movement and measuring a parameter of flow of the liquid through the orifice, and then f) determining a relationship between the flow parameter and the piston movement parameter, the relationship being indicative of the rheological properties of the liquid.

In one embodiment of the method of the invention, the piston movement parameter is at least one of the timing and the speed of piston strokes, while the differential pressure across the orifice is measured as the flow parameter.

In another embodiment of the method, the displacement of the piston strokes is measured as a function of time and a constant pressure is applied on the piston; the parameter measured is the average flow rate through the orifice; the flow parameter measured is the time for a predetermined amount of the sample to flow through the orifice.

BRIEF DESCRIPTION OF THE DRAWINGS

The invention will be explained in more detail by the following detailed description, including the known best mode of the invention, the description to be taken in conjunction with the drawings in which.

DETAILED DESCRIPTION OF THE INVENTION

Figure 1:
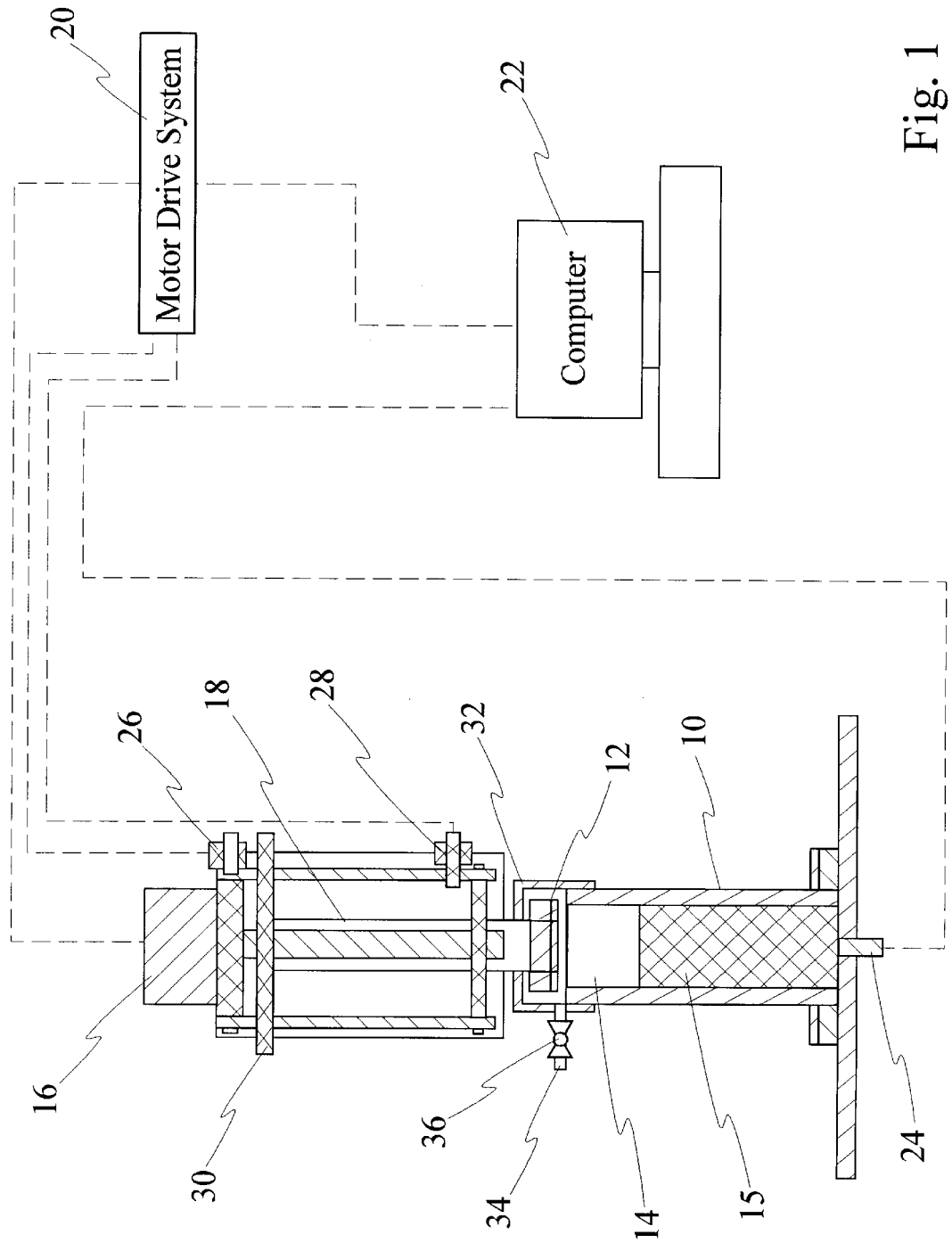
FIG. 1 represents schematically an exemplary apparatus of the invention.

As seen in FIG. 1, the apparatus has a barrel 10 with a piston 12 mounted slidably within the barrel such that it defines a space 14 which is filled with a liquid 15 to be tested. The piston is connected to a drive rod 18, which is driven by a motor 16. A motor control unit 20 is provided for controlling the timing and the speed of the downward stroke of the piston 12 towards the liquid 15.

The apparatus has a data acquisition system 22, which is connected to a pressure sensor 24, located at the bottom of the barrel 10. The motor control unit is connected to the motor 16, to an upper limit sensor 26 and to a lower limit sensor 28. A positioning plate 30 is mounted on the drive rod 18 to engage the upper and lower limit sensor during the upward stroke and downward stroke respectively.

The barrel 10 has a detachable end cap 32 which seals the barrel when mounted thereon and when detached, enables a sample of the liquid to be placed in the barrel. A tubing 34 with a vent valve 36 is mounted on the end cap to enable the space within the end cap to be open to atmospheric pressure.

Figure 2:
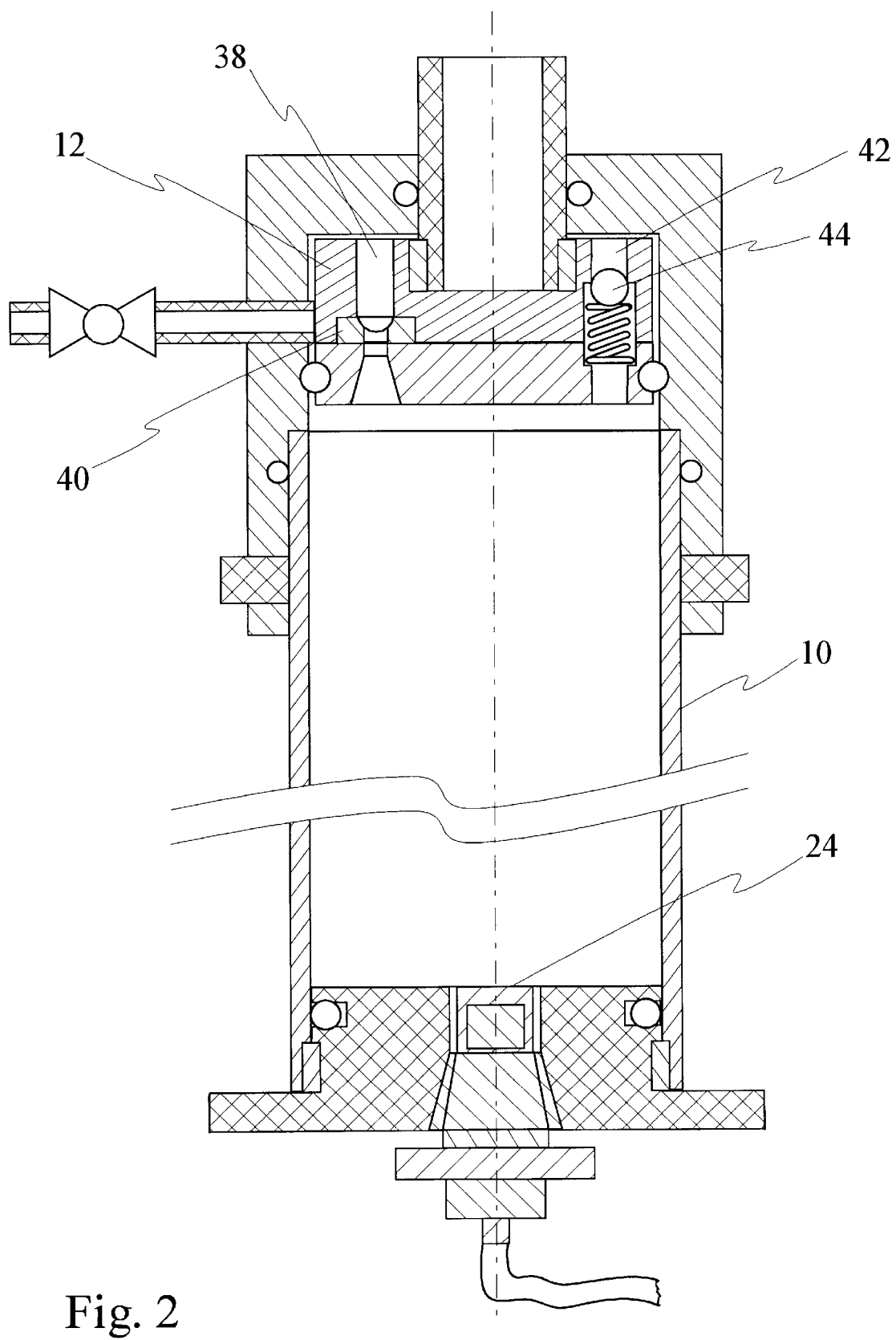
FIG. 2 is a partial cross-sectional view of the apparatus.

The piston 12 is shown in more detail in FIG. 2 wherein like reference numerals denote like elements as in FIG. 1. The piston has a channel 38 adapted to accommodate a detachable orifice plate 40. The piston also has a return channel 42 with a return valve, embodied by a spring-biased ball valve 44.

In operation, the end cap 32 is lifted and the barrel 10 is filled with a liquid tested (fracturing gel) until the level of the liquid is close to the top but still enables the piston to close the barrel before it touches the liquid. Sufficient space must be let between the top level of the gel and the piston head at the start of the test to compensate for the immersion of the piston and rod within the gel when the piston head reaches the bottom of the barrel. The piston is then lowered into the barrel 10 and the end cap 32 is replaced. The vent valve 36 is open so that the pressure above the piston is atmospheric. The piston is operated to move downwards at a predetermined constant speed. The liquid 15 is pressurized and is forced to flow through the orifice in the plate 40. The pressure of the liquid is monitored by means of the pressure sensor 24. The pressure drop across the orifice is determined as a difference between the pressure reading of the sensor 24 and the atmospheric pressure.

When the downward stroke is finished, most of the liquid will have passed through the orifice and will be contained above the piston. The vent valve 36 is now closed. When the piston is moved upwards, the liquid is forced to flow through the return channel 42 with the valve 44 (and partly through the channel 38 and the orifice 40) back into the initial space 14 in the barrel 10. The operation can now be repeated a number of times, i.e. the vent valve 36 is opened, the piston is moved downwards at a predetermined speed etc. It will be shown that the speed of the downward piston stroke can be changed from one stroke to another, but also during one downward stroke.

In an alternative embodiment, the control unit may be a pressure control unit for controlling the pressure, rather than speed, of the piston during its downward stroke. The timing of the sequential strokes would still be controlled as above. The duration of the successive piston strokes would be the parameter of flow of the liquid. The function of the stroke displacement versus the piston pressure would constitute the rheological "signature" of the liquid measured.

It will be noted that in the preferred embodiment of the invention, the liquid is stationary while the piston with the orifice moves against it. This provision is advantageous in that it reduces the occurrence of the slippage and deformation of the liquid against the walls of the chamber, which would take place if the liquid were pressed through a stationary orifice. Advantageously, the embodiment provides easy cleaning of the chamber and more accurate control of flow rate compared with a pump. It should be noted that there is still slip at the wall of the orifice, however, the pressure drop across the orifice is mostly due to converging flow. The material is deformed completely during converging flow.

The flow restriction from the diameter of the chamber (barrel) to the diameter of the orifice gives rise to the elongation (longitudinal deformation) of the gel which in turn causes a change of the rheology of the non-Newtonian liquid. It is advantageous to have a relatively large ratio of these diameters, a so-called contraction ratio. The ratio should preferably be at least 15 for a typical fracturing gel. The design as illustrated in FIGS. 1 and 2 is amenable to an easy replacement of the orifice plate, by removal of the piston, depending on the characteristics of the liquid tested.

As mentioned above, in an alternative design the orifice can be stationary i.e. mounted in the bottom or the top of the barrel rather than in the piston. The liquid is forced by the piston through the orifice and the pressure difference across the orifice can be measured. The liquid would be returned to the barrel through an outside return conduit by means of a pump.

Figure 5:
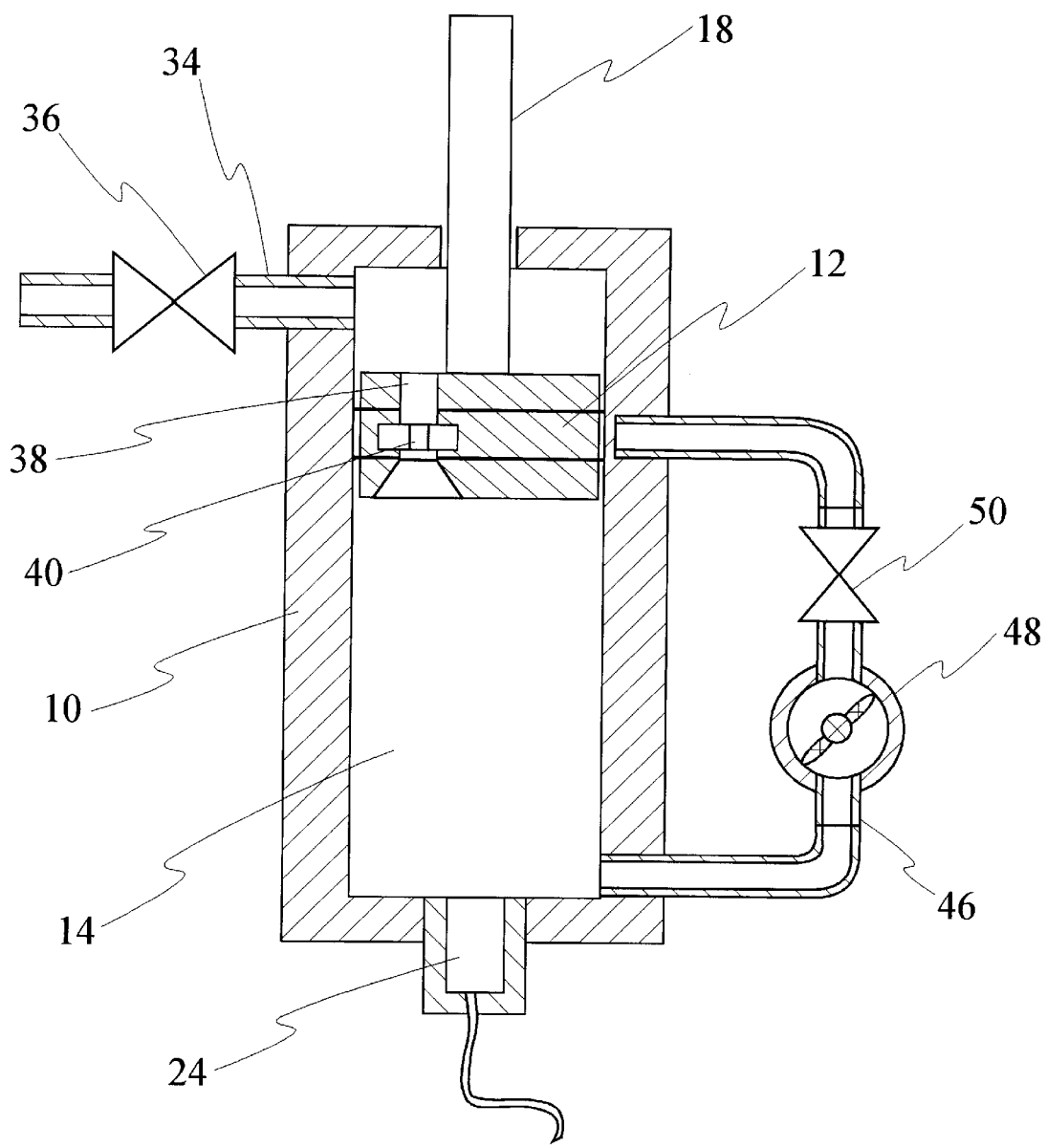
FIG. 5 is a schematical representation of an alternative embodiment of the apparatus.

In another alternative design, illustrated schematically in FIG. 5, the passage 38 with the orifice plate 40 is still provided in the movable piston, but a return passage 46 is provided outside the barrel 10. The passage has a pump 48 and a valve 50 thereon. During the downward stroke of the piston 12, the valve 50 is closed. When the downward stroke is finished, the valve 50 is opened. The liquid, which has now passed through the orifice and is placed above the piston 12 is pumped through the return passage 46 to the initially occupied space 14 in the barrel 10 for another cycle as described above. As the liquid is pumped, the piston 18 is raised.

It may be advantageous to provide the return passage of a relatively large diameter to minimize the shear forces on the liquid tested. For the same reason, it may be advantageous to use a low-shear pump, e.g. a peristaltic pump. In the embodiment illustrated in FIG. 1 and FIG. 2, it is easily conceivable to modify the design so that the measurement is carried out not only on the downward stroke, but also on the upward stroke of the piston. In this case, no separate return passage is needed.

EXAMPLE 1.

A hydroxypropyl guar (HPG) gel was prepared as follows:

One liter of de-ionized water was placed in a vessel and mixed to obtain a deep vortex. While mixing, the following was added to the water:

20 ml. of a clay stabilizer (M117)

0.5 g of a bactericidal agent (quaternary amine) (M76)

2.0 ml of a proprietary surfactant (F75)

0.15 g of a boric acid cross-linker (L10) (which was mixed for approximately 3 minutes)

6.0 ml of a proprietary guar gum gelling agent (J424) which was mixed for 10 minutes)

7.5 ml of a sodium hydroxide cross-linker activator. (J221)

The manufacturer of M177, L10 and J221 was Van Watters and Rogers (Kirkland, Wash., USA). The manufacturer of M76, F75 and J424 was Dowell (Sugarland, Tex., USA).

The gelling agent concentration determines the gel strength when the gel is prepared under optimum conditions.

Ten consecutive runs were performed on the apparatus as illustrated in FIG. 1 and FIG. 2. The motor control unit was programmed to advance at five different rates: 1.23 cm/sec, 0.98 cm/sec, 0.74, 0.45 and 0.25 cm/sec during a single downward stroke. The pressure drop across the orifice was plotted in FIGS. 3a–3j versus time for each of the 10 downward strokes. The sequence of piston speeds was the same at each downward stroke.

In FIGS. 3a–3j, the numbers above each peak indicate the piston rate of advance (speed). The time at which each downward stroke started (Tstart) is also indicated in the FIGS. 3a–3j, and the time increment (DT) between consecutive downward strokes is shown.

Figure 3A:
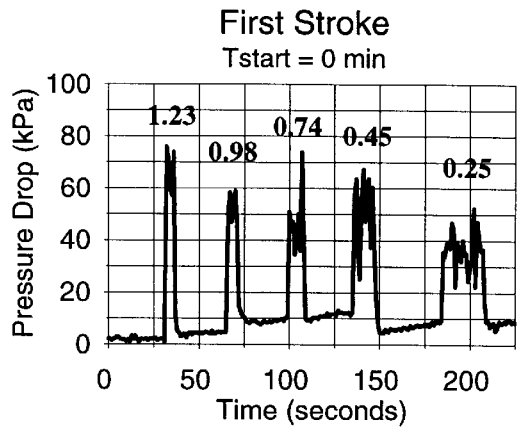
FIGS. 3a–3j are graphs illustrating the pressure-timing relationship determined for an exemplary liquid, a water-based gel, using the apparatus and method of the invention.
Figure 3B:
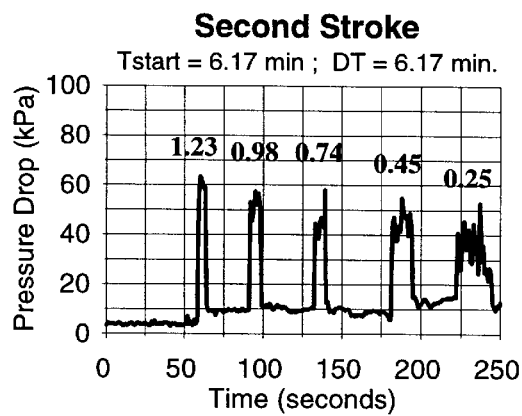
Figure 3C:
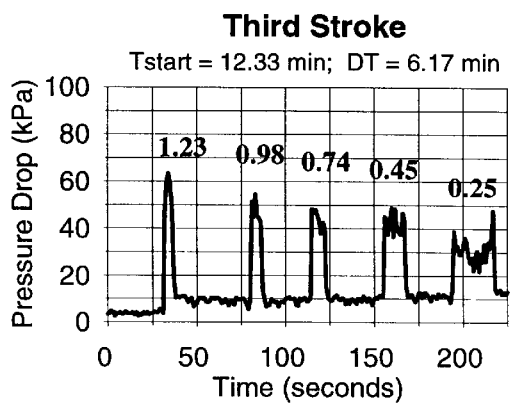
Figure 3D:
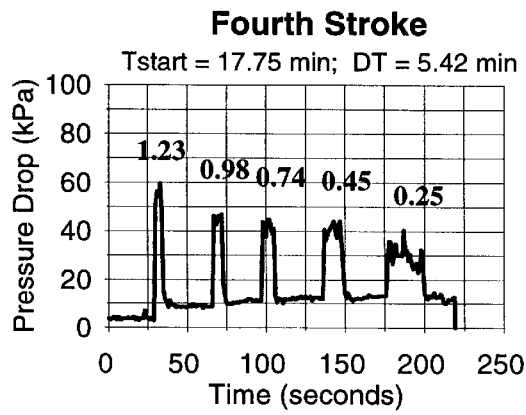
Figure 3E:
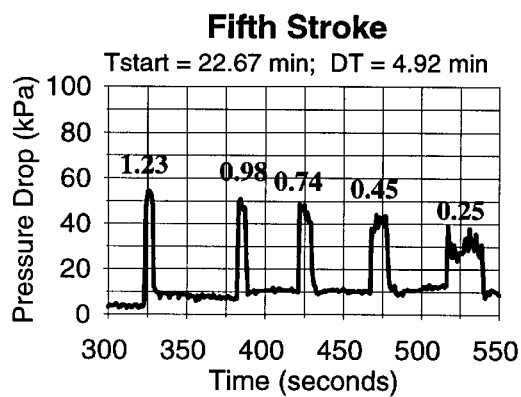
Figure 3F:
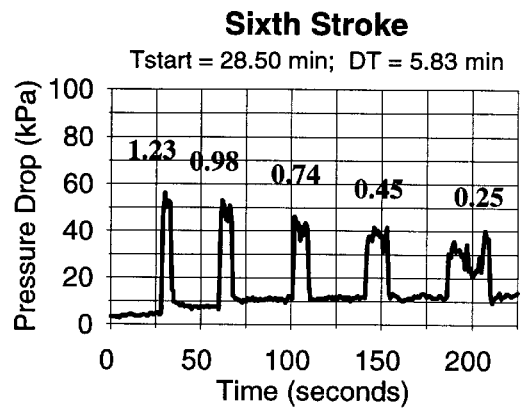
Figure 3G:
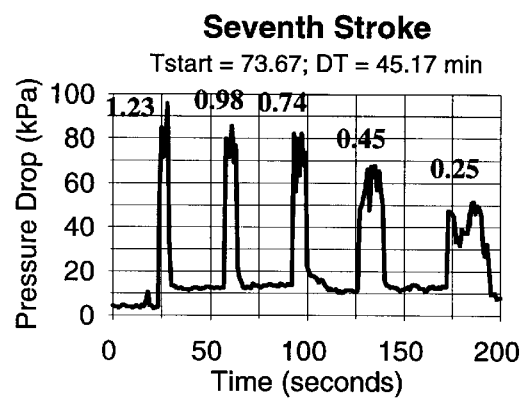
Figure 3H:
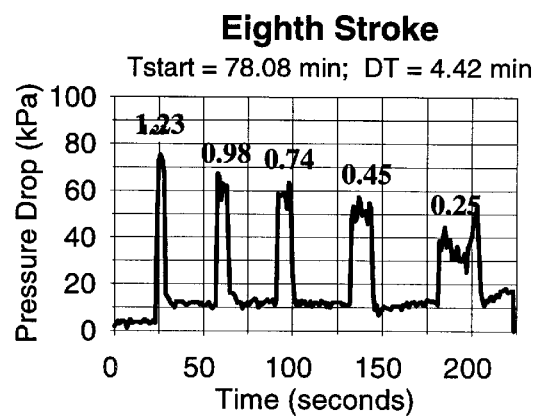
Figure 3I:
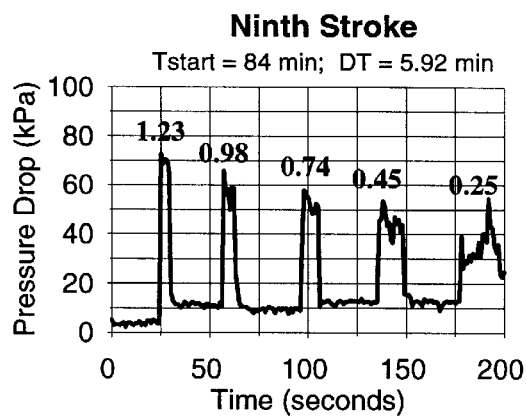
Figure 3J:
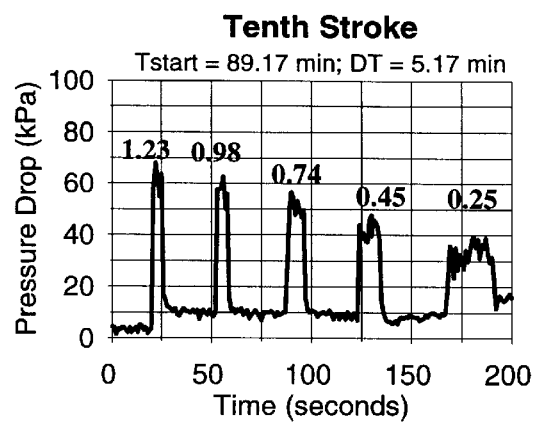
Figure 4A:
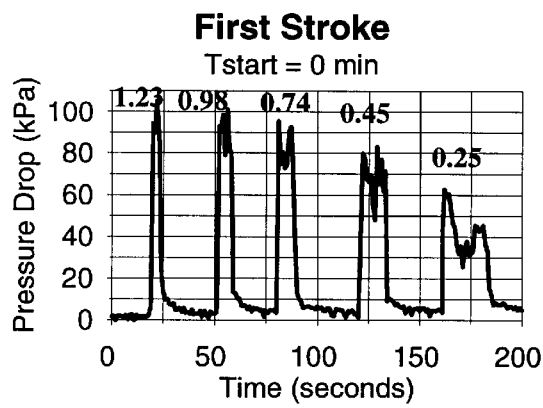
FIGS. 4a–4i are graphs illustrating the pressure-timing relationship determined for a diesel-based gel, using the apparatus and method of the invention.
Figure 4B:
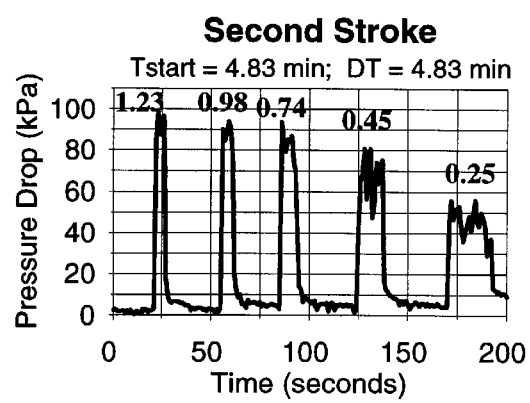
Figure 4C:
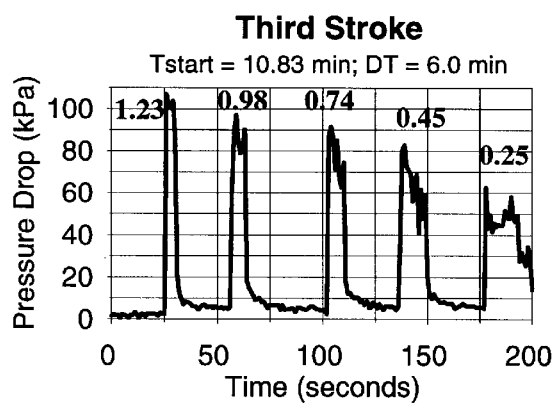
Figure 4D:
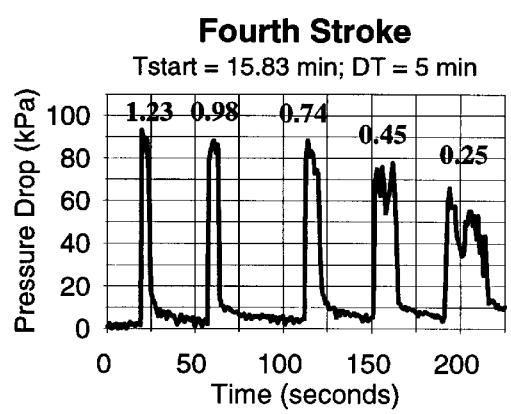
Figure 4E:
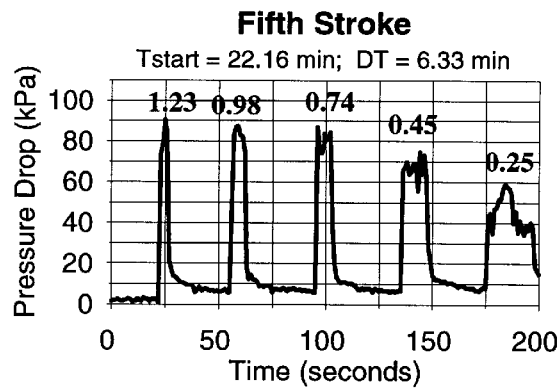
Figure 4F:
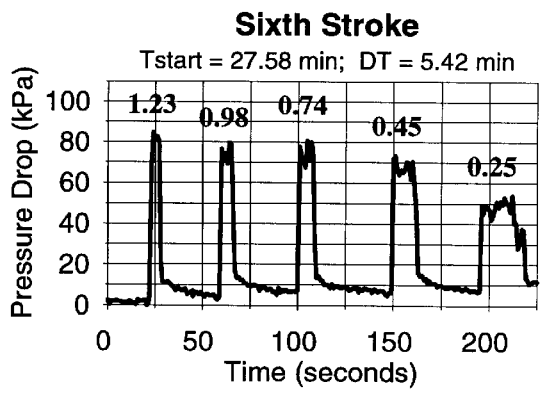
Figure 4G:
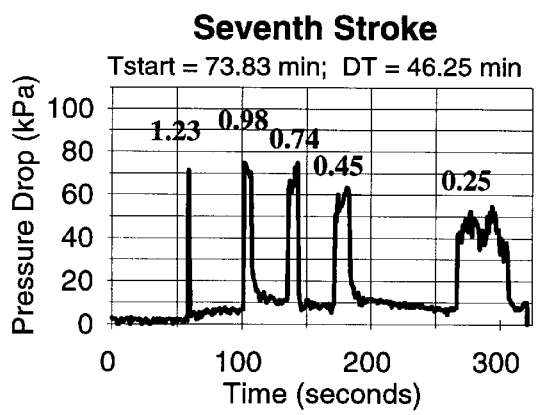
Figure 4H:
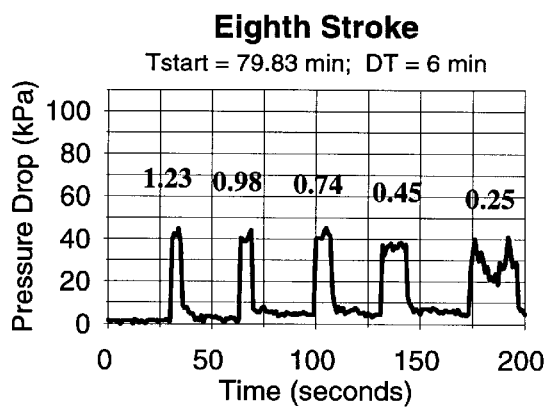
Figure 4I:
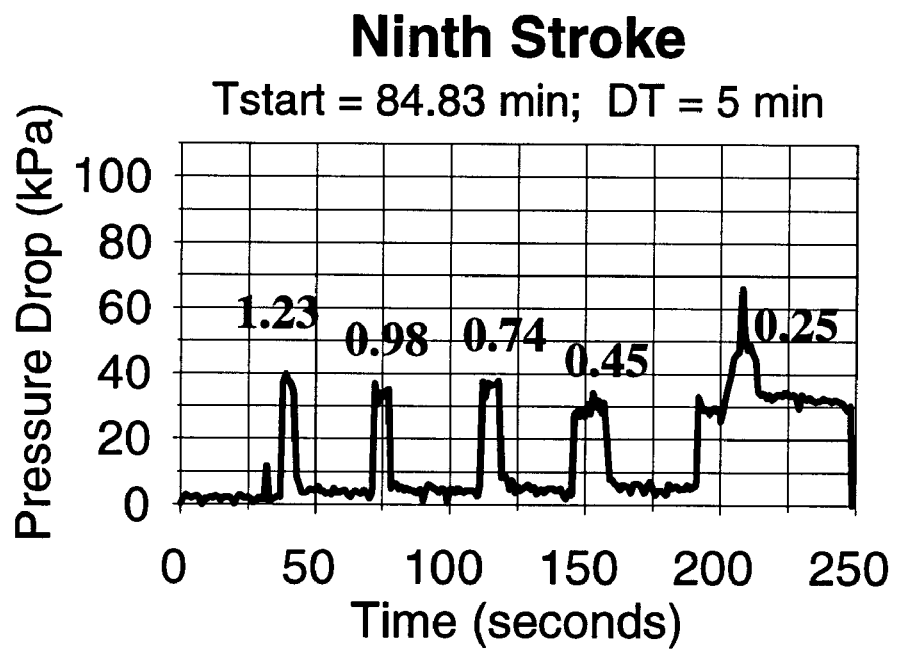

It will be seen that the relationship between the pressure drop across the orifice and the speed of the piston stroke varies from one stroke to another and depends on the degree of deformation imparted on the sample as a result of its compression during the passage through the orifice, as well as on the degree of relaxation gained with time elapsed after each such passage. It will be observed in FIGS. 3a–3j that the peaks diminish from the first through the fourth stroke, reach a plateau at the fifth and sixth stroke and increase at the seventh stroke (FIG. 3g). This may be attributed to a longer period of relaxation between the sixth and the seventh stroke.

EXAMPLE 2

A hydrocarbon-based gel was prepared by mixing orthophosphate esters with aluminum salts to diesel oil as follows:

One liter of diesel oil was placed in a vessel and stirred with a mixer to obtain a deep vortex;

In a separate container, 10 ml of an activator solution was prepared by mixing 5 parts of poly aluminum chloride (J601) with 1 part of sodium acetate (J602). While stirring the diesel oil, 10 ml of the activator solution and 10 ml of phosphate ester (J452) were added simultaneously by injecting into the diesel with separate syringes. The injection lasted approximately one minute.

The manufacturer of J601 and J602 was Van Watters and Rogers (Kirkland, Wash., USA). The manufacturer of J452 was Dowell (Sugarland, Tex., USA).

Ten consecutive runs were performed on the apparatus as illustrated in FIG. 1 and FIG. 2. The motor control unit was programmed to advance at five different rates: 1.23 cm/sec, 0.98 cm/sec, 0.74, 0.45 and 0.25 cm/sec during a single downward stroke. The pressure drop across the orifice was plotted in FIGS. 4a–4i versus time for each of the 10 downward strokes. The sequence of piston speeds was the same at each downward stroke.

In FIGS. 4a–4i, the numbers above each peak indicate the piston rate of advance (speed). The time at which each downward stroke started (Tstart) is also indicated in the FIGS. 4a–4i, and the time increment (DT) between consecutive downward strokes is shown.

The results, which constitute a distinct rheological "signature" of the gel, indicate that for the particular diesel-based gel the pressure drop at a given rate of piston advance decreased sharply after the sixth stroke even though the gel was not deformed for 46 minutes. This behaviour contrasted with the water-based gel (Example 1) which gained strength after a time increment of 45 minutes. The diesel-based gel lost its strength after several deformations.

Regardless of the actual numeric values of the pressure-time function for the particular gel, it is important that each gel was found to exhibit repetitively a similar function when tested in the same conditions, i.e. stroke speed and timing schedule. The gel strength changes with time and with deformation. After several strokes the test is repeatable from one test to the next since the viscosity and strength of the gel has stabilized. It is therefore possible, unlike in prior art approaches, to establish a characteristic "signature" function for a particular liquid by carrying out the test in specific conditions, and then test fluid prepared in the field in the same conditions (this applies basically to non-Newtonian liquids). A similar or identical "signature" relationship between the test parameters will most likely indicate a liquid with similar or identical rheological properties.

Similarly to the apparatus of the invention, the method as described is a non-limiting example. Modifications are possible, in line with the type of the apparatus used. E.g. instead of maintaining a predetermined speed of the piston downward stroke, the pressure on the piston can be controlled and the flow rate through the orifice can be determined as a "signature" function of the rheological properties of the liquid tested.

It is a feature of the invention that a single sample of a non-Newtonian liquid, e.g. a fracturing gel, can be tested several times with easy reloading. To flow through the orifice, the gel must first yield and then elongate along the flow axis. The polymer molecules of the gel are then stretched which leads to a significant tensile stresses along the flow lines and consequently to a significant pressure drop at the entrance to the orifice. The tensile stress is dependent on the molecular weight and flexibility of the polymer chains, and therefore can serve as an indication of the degree of cross-linking between chains. The tests show that the elongational strength of the gel depends on the number of times it is deformed. This dependence can be expressed by the time required for the cross-links to be broken and reformed.

It is an advantage of the invention that the apparatus can be reloaded with the sample several times without the need for handling the fluid, thus eliminating the possibility of contamination.

We claim:

1. An apparatus for evaluating the rheological properties of a liquid, the apparatus comprising:

a chamber for accommodating a quantity of a liquid to be evaluated, a piston slidably movable within said chamber, a drive means for moving said piston, a control means associated with said drive means for controlling at least one parameter Of the movement of said piston, an orifice in fluid communication with the chamber such that the liquid can pass through the orifice when the liquid is forced against it by a movement of the piston, a separate return flow passage for returning the liquid expressed through the orifice back to the chamber, measurement means for measuring a parameter of the flow of the liquid through the orifice, and data acquisition and processing means for evaluating said flow parameter as a function of the piston movement parameter, the function being indicative of the rheological properties of the liquid.

2. The apparatus according to claim 1, wherein the separate return flow passage includes a valve for controlling the return flow of the liquid.

3. The apparatus according to claim 1 wherein said control means are piston stroke rate control means.

4. The apparatus according to claim 3 wherein said measurement means are means for measuring the differential pressure across said orifice.

5. The apparatus according to claim 1 wherein said control means is a piston pressure control means.

6. The apparatus according to claim 5 wherein said measurement means is a piston stroke displacement measurement means.

7. The apparatus according to claim 1 where said orifice is associated with said piston.

8. The apparatus according to claim 1 wherein said orifice excludes a capillary having a length substantially larger than a diameter.

9. The apparatus according to claim 1 wherein the separate return flow passage is larger in diameter than the orifice.

10. An apparatus for evaluating the rheological properties of a liquid, the apparatus comprising:

a closable barrel adapted to receive a quantity of a liquid to be evaluated, the barrel having a first end and a second distal end, a piston slidable in said barrel between said first end and said second end, thus defining a first and a second chamber between said piston and the respective ends of the barrel, drive means for moving said piston between the first and the second end, control means associated with the drive means for controlling the speed and timing of the piston movement, an orifice associated with the piston and adapted for the liquid to pass therethrough from said first chamber to the second chamber when said liquid is pressured by the movement of the piston against it, a separate return flow means for enabling the flow of the liquid back to the first chamber when the stroke of the piston is reversed, differential pressure measurement means for measuring the pressure drop across the orifice during the flow of the liquid through the orifice, and data acquisition and processing means for determining a relationship between the differential pressure and the at least one of the timing and the speed of the piston strokes, the relationship being indicative of rheological properties of the liquid.

11. The apparatus according to claim 10 wherein said separate return flow means comprises a passage in said piston.

12. The apparatus according to claim 10 wherein said piston has a passage with said orifice therein and another passage having a valve to control the return flow of the liquid.

13. The apparatus according to claim 10 wherein said separate return flow means comprises a conduit disposed outside of said barrel and propelling means for forcing said liquid from said second chamber to said first chamber through said conduit.

14. A method for evaluating the rheological properties of a liquid utilizing an apparatus having a chamber for accommodating a quantity of a liquid to be evaluated, a piston slidably movable within the chamber, and an orifice in fluid communication with the chamber such that the liquid can pass through the orifice when the liquid is forced against it by a movement of the piston, the method comprising a) placing a sample of the liquid to be evaluated in the chamber, b) forcing the sample to flow from the chamber through the orifice by way of a movement of said piston, c) causing the sample to flow back into the chamber through a separate retrn flow passage, d) repeating steps b) and c) while e) controlling at least one parameter of the piston movement and measuring a parameter of flow of the liquid through the orifice, and then f) determining a relationship between the flow parameter and the piston movement parameter, the relationship being indicative of the rheological properties of the liquid.

15. The method according to claim 14 wherein the at least one parameter of the piston movement is the piston stroke rate.

16. The method according to claim 15 wherein the parameter of flow of the liquid is a pressure difference across said orifice.

17. The method according to claim 14 wherein said at least one parameter of the piston movement is the piston pressure.

18. The method of claim 14 wherein said orifice is associated with said piston and wherein said liquid remains stationary during the piston advance.

19. The method of claim 14 wherein said separate return flow means is associated with said piston.

20. The method of claim 14 wherein the separate return flow means comprises a valve for controlling the return flow of the liquid.

21. The method according to claim 14 wherein said orifice excludes a capillary having a length substantially larger than a diameter.

22. The method according to claim 14 wherein the separate return flow passage is larger in diameter than the orifice.

23. A method for evaluating the rheological properties of a liquid utilizing an apparatus having a chamber for accommodating a quantity of a liquid to be evaluated, a piston slidably movable within the chamber, and an orifice in fluid communication with the chamber such that the liquid can pass through the orifice when the liquid is forced against it by a movement of the piston, the method comprising a) placing a sample of the liquid to be evaluated in the chamber, b) forcing the sample to flow from the chamber through the orifice and back to the chamber through a separate return flow passage, c) repeating step b) a number of times while d) controlling at least one parameter of the piston movement and measuring a parameter of flow of the liquid through the orifice, and then e) determining a relationship between the flow parameter and the piston movement parameter, the relationship being indicative of the rheological properties of the liquid.

* * * * *